US012337333B2

(12) United States Patent
Zhu et al.

(10) Patent No.: US 12,337,333 B2
(45) Date of Patent: Jun. 24, 2025

(54) NEGATIVE ION GENERATING DEVICE AND AIR PURIFIER

(71) Applicants: BEIJING XIAOMI MOBILE SOFTWARE CO., LTD., Beijing (CN); BEIJING SMARTMI TECHNOLOGY CO., LTD., Beijing (CN)

(72) Inventors: Kenan Zhu, Beijing (CN); Lei Jia, Beijing (CN); Guang Xi, Beijing (CN)

(73) Assignees: BEIJING XIAOMI MOBILE SOFTWARE CO., LTD., Beijing (CN); BEIJING SMARTMI TECHNOLOGY CO., LTD., Beijing (CN)

( * ) Notice: Subject to any disclaimer, the term of this patent is extended or adjusted under 35 U.S.C. 154(b) by 436 days.

(21) Appl. No.: 17/874,179

(22) Filed: Jul. 26, 2022

(65) Prior Publication Data

US 2023/0338970 A1 Oct. 26, 2023

(30) Foreign Application Priority Data

Apr. 25, 2022 (CN) .......................... 202210440588.7

(51) Int. Cl.
*B03C 3/74* (2006.01)
*B03C 3/41* (2006.01)
(Continued)

(52) U.S. Cl.
CPC ................ *B03C 3/746* (2013.01); *B03C 3/41* (2013.01); *B08B 1/165* (2024.01); *B08B 1/30* (2024.01); *H01T 23/00* (2013.01); *B03C 2201/10* (2013.01)

(58) Field of Classification Search
CPC .... B03C 3/41; B03C 3/32; B03C 3/38; B03C 3/743; B03C 3/746; B03C 2201/10;
(Continued)

(56) References Cited

U.S. PATENT DOCUMENTS 5,973,905 A * 10/1999 Shaw ...................... H01T 23/00
361/231
6,785,114 B2 * 8/2004 Gorczyca .................. B03C 3/12
361/231
(Continued)

FOREIGN PATENT DOCUMENTS

CN 104006458 A 8/2014
CN 203816953 U 9/2014
(Continued)

OTHER PUBLICATIONS

Request for the Submission of an Opinion issued in Application No. 10-2022-0094241 dated Mar. 19, 2024 with English translation, (10p).

(Continued)

*Primary Examiner* — Jennifer Dieterle
*Assistant Examiner* — Sonji Turner
(74) *Attorney, Agent, or Firm* — Arch & Lake LLP

(57) ABSTRACT

The present disclosure relates to a negative ion generating device and an air purifier. The negative ion generating device includes a housing, a negative ion assembly, and a cleaning assembly. The negative ion assembly is arranged to the housing, and the negative ion assembly includes a conductive fiber brush. The cleaning assembly is arranged to the housing, the cleaning assembly includes a driving mechanism and a cleaning member, and the cleaning member can move under action of the power provided by the driving mechanism, and contact or separate from the conductive fiber brush during movement.

19 Claims, 5 Drawing Sheets

(51) Int. Cl.
 *B08B 1/16* (2024.01)
 *B08B 1/30* (2024.01)
 *H01T 23/00* (2006.01)

(58) Field of Classification Search
 CPC .. B08B 1/165; B08B 1/30; B08B 1/12; B08B 3/08; F24F 8/30; F24F 8/90; A61L 9/22; A46B 15/0024; A46D 1/0207; H01T 23/00; H01T 23/06; H01T 19/04; Y02A 50/20
 See application file for complete search history.

(56) References Cited

U.S. PATENT DOCUMENTS

| | | | | |
|---|---|---|---|---|
| 9,847,623 | B2* | 12/2017 | Sunshine | H01T 23/00 |
| 10,319,569 | B2* | 6/2019 | Waddell | B08B 1/32 |
| 10,748,733 | B2* | 8/2020 | Nishida | B60H 3/0071 |
| 10,910,186 | B2* | 2/2021 | Nishida | H01J 27/22 |
| 10,980,909 | B2* | 4/2021 | Okano | B60H 3/0071 |
| 11,344,922 | B2* | 5/2022 | Waddell | B03C 3/41 |
| 11,581,709 | B2* | 2/2023 | Waddell | H01T 23/00 |
| 2015/0013541 | A1* | 1/2015 | Vandenbelt | B03C 3/47 96/98 |
| 2016/0221002 | A1* | 8/2016 | Lin | B03C 3/363 |
| 2018/0243462 | A1 | 8/2018 | Okano et al. | |
| 2020/0388994 | A1* | 12/2020 | Waddell | B01D 53/32 |
| 2021/0091542 | A1* | 3/2021 | Kim | H01T 23/00 |

FOREIGN PATENT DOCUMENTS

| | | |
|---|---|---|
| CN | 212429274 U | 1/2021 |
| JP | 2005046616 A | 2/2005 |
| JP | 2005276603 A | 10/2005 |
| JP | 2007280701 A | 10/2007 |
| WO | 2019157419 A1 | 8/2019 |
| WO | 2019225090 A1 | 11/2019 |
| WO | 2020013144 A1 | 1/2020 |

OTHER PUBLICATIONS

OA for CN Application No. 202210440588.7 dated Oct. 10, 2023 with English translation, (21p).

OA for JP Application No. 2022-121855 dated Aug. 22, 2023 with English translation, (16p).

Extended European Search report issued in European Patent Application No. 22187642.8 dated May 11, 2023, (7p).

* cited by examiner

NEGATIVE ION GENERATING DEVICE AND AIR PURIFIER

CROSS-REFERENCE TO RELATED APPLICATIONS

This application claims priority to Chinese Patent Application No. 202210440588.7 filed on Apr. 25, 2022, the entire content of which is incorporated herein by reference for all purposes.

FIELD

The present disclosure relates a field of air purifying technologies, and more particularly to a negative ion generating device and an air layer.

BACKGROUND

The negative ion generating device is a device that generates negative air ions. The device can process an input current to obtain a DC (direct current) negative high voltage current, and then couple the DC negative high voltage current to a release tip made of metal or carbon elements.

The negative ion generating device utilizes the high-voltage direct current at the tip to generate high corona and release a large number of electrons at high speed. Since an existence life of electrons is only nanoseconds, the electrons cannot exist in the air for a long time, and the electrons are immediately captured by the oxygen molecules in the air, thereby generating negative air ions.

SUMMARY

According to a first aspect of the present disclosure, a negative ion generating device is provided, which includes a housing; a negative ion assembly arranged to the housing, the negative ion assembly being configured to produce a negative ion, the negative ion assembly including a conductive fiber brush; and a cleaning assembly arranged to the housing, the cleaning assembly including a driving mechanism and a cleaning member coupled to a power output end of the driving mechanism, the driving mechanism being configured to provide power, the cleaning member being capable of moving under action of the power provided by the driving mechanism, and contacting or separating from the conductive fiber brush during movement.

According to a second aspect of the present disclosure, an air purifier is provided, which includes a negative ion generating device and a bracket. The negative ion generating device is fixed through the bracket. The negative ion generating device includes a housing; a negative ion assembly arranged to the housing, the negative ion assembly being configured to produce a negative ion, the negative ion assembly including a conductive fiber brush; and a cleaning assembly arranged to the housing, the cleaning assembly including a driving mechanism and a cleaning member coupled to a power output end of the driving mechanism, the driving mechanism being configured to provide power, the cleaning member being capable of moving under action of the power provided by the driving mechanism, and contacting or separating from the conductive fiber brush during movement

BRIEF DESCRIPTION OF THE DRAWINGS

The accompanying drawings herein are incorporated into the specification and constitute a part of the specification. Theses accompanying drawings illustrate embodiments conform to the present disclosure and are used to explain the principles of the present disclosure together with the specification.

BRIEF DESCRIPTION OF THE DRAWINGS

Figure 1:
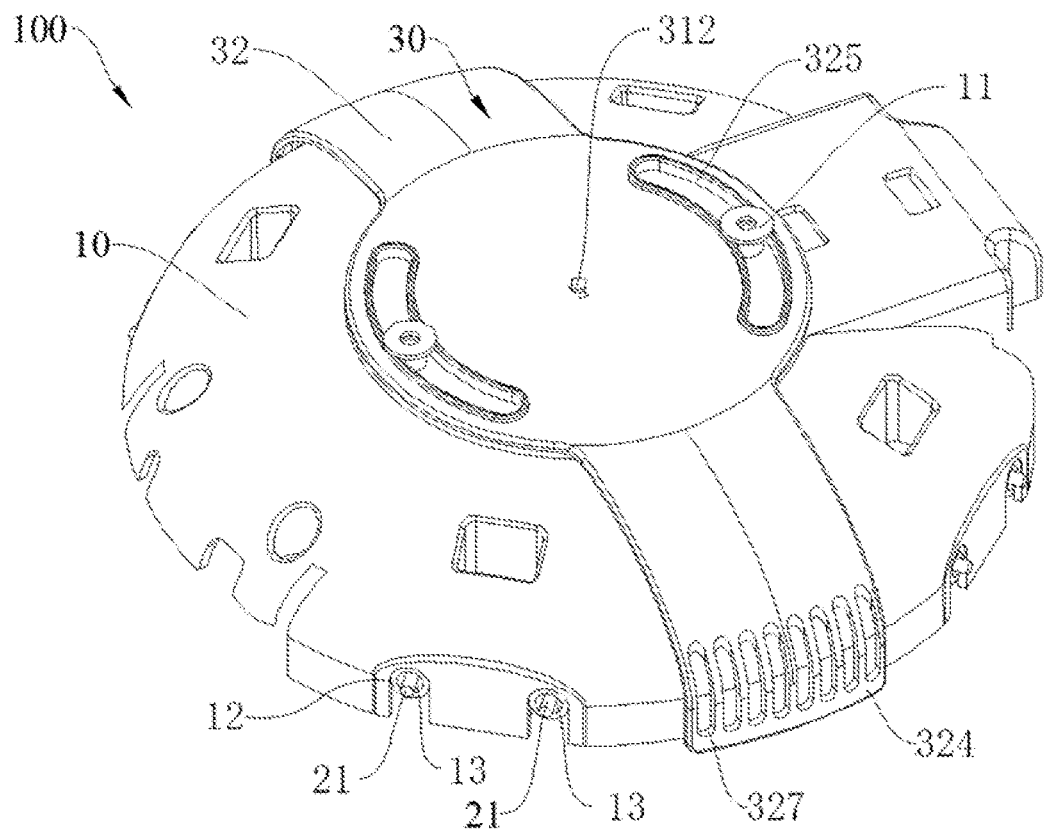
FIG. 1 is a perspective view of a negative ion generating device illustrated according to one or more examples of the present disclosure.

Exemplary embodiments will be illustrated in detail herein, and the examples thereof are shown in the accompanying drawings. When the following description refers to the accompanying drawings, unless otherwise specified, the same or similar elements are denoted by the same numerals in the different accompanying drawings. Implementations described in the exemplary embodiments do not represent all implementations consistent with the present disclosure. On the contrary, they are merely examples of a device and a method consistent with some aspects of the present disclosure, as elaborated in the scope of the claims.

Terms used in the present disclosure are merely for describing specific examples and are not intended to limit the present disclosure. The singular forms "one", "the", and "this" used in the present disclosure and the appended claims are also intended to include a multiple form, unless other meanings are clearly represented in the context. It should also be understood that the term "and/or" used in the present disclosure refers to any or all of possible combinations including one or more associated listed items.

Reference throughout this specification to "one embodiment," "an embodiment," "an example," "some embodiments," "some examples," or similar language means that a particular feature, structure, or characteristic described is included in at least one embodiment or example. Features, structures, elements, or characteristics described in connection with one or some embodiments are also applicable to other embodiments, unless expressly specified otherwise.

It should be understood that although terms "first", "second", "third", and the like are used in the present disclosure to describe various information, the information is not limited to the terms. These terms are merely used to differentiate information of a same type. For example, without departing from the scope of the present disclosure, first information is also referred to as second information, and similarly the second information is also referred to as the first information. Depending on the context, for example, the term "if" used herein may be explained as "when" or "while", or "in response to . . . , it is determined that".

With the rapid development of industry, air quality is facing serious pollution. In daily life, air purifiers attract more and more attention, and an important component of air purifiers is the negative ion generating device.

In the related art, the negative ion generating device uses a high-voltage direct current at the tip to generate high corona, and emits a large number of electrons at a high speed. However, the electrons cannot exist in the air for a long time (the existence life of electrons is only nanoseconds), and the electrons are immediately captured by oxygen molecules in the air, to generate negative air ions.

The negative air ions are combined with soot, dust and particles in the air. Due to the action of gravity, the electrostatically charged soot, dust and particles are settled, which can achieve the purpose of dust removal. Users live and work in an environment with abundant negative air ions, which has good effects, e.g.:

lung function improvement, after inhaling negative ions for 30 minutes, the amount of oxygen that can be absorbed by human lungs increasing by 20%, and carbon dioxide being excreted by 15% more;

myocardial function improvement, negative ions having obvious antihypertensive effect, being capable of improving myocardial function and increasing myocardial vitality;

sleep improvement, after the action of negative ions, it being capable of making people's spirits up, work efficiency improved, and it being also capable of improving sleep, with obvious sedative and hypnotic effects;

metabolism promotion, negative ions being capable of activating various enzymes in the body and promoting metabolism;

disease resistance enhancement, negative ions being capable of changing the body's reactivity, activating the function of the reticuloendothelial system, and enhancing the body's immunity; and bactericidal function, negative ions easily adsorbing bacteria, causing structural changes and energy transfer, resulting in bacterial disease and death.

In the related art, the conductive fiber brush is used as the negative ion generating source, and the conductive fiber brush is easy to manufacture, has a long service life, can improve the negative ion generating efficiency, and can realize improved antibacterial and sterilizing functions by distributing particles within activated carbon fibers and applying voltage to them.

However, the closer it is to the source of negative ions, the higher the concentration of negative ions, and some of the negative ions will actively combine with air pollutants, causing the pollutants to be negatively charged to be condensed and settled or adsorbed on the conductive fiber brush, resulting in blocking of the conductive fiber brush to reduce its generation efficiency of negative ions, thereby reducing its use effect.

In the related art, the negative ion generating device uses a conductive fiber brush as the negative ion generating source, and the conductive fiber brush is easy to manufacture, has a long service life, can improve the negative ion generating efficiency, and has antibacterial and sterilizing functions.

However, the conductive fiber brush is used as the source of negative ions, and the air pollutants around the conductive fiber brush are easily condensed and settled or adsorbed on the conductive fiber brush after being negatively charged, thereby causing the conductive fiber brush to be blocked and reducing the generation efficiency of negative ions by the conductive fiber brush, and reducing the use effect of the conductive fiber brush.

In order to overcome problems existing in the related art, the present disclosure provide a negative ion generating device and an air purifier.

As illustrated in FIGS. 1-8, according to a first aspect of embodiments of the present disclosure, a negative ion generating device 100 is provided. The negative ion generating device 100 includes a housing 10, a negative ion assembly 20, and a cleaning assembly 30.

The negative ion assembly 20 is arranged to the housing 10, the negative ion assembly 20 is configured to produce a negative ion, and the negative ion assembly 20 includes a conductive fiber brush 21.

Specifically, the conductive fiber brush 21 is arranged to the housing 10, and the conductive fiber brush 21 extends away from the housing 10 in a radial direction of the housing 10.

The cleaning assembly 30 is arranged to the housing 10, and the cleaning assembly 30 includes a driving mechanism 31 and a cleaning member 32 coupled to a power output end of the driving mechanism 31. The driving mechanism 31 is configured to provide power, the cleaning member 32 can move under action of the power provided by the driving mechanism 31, and contact or separate from the conductive fiber brush during movement.

In the present disclosure, as illustrated in FIGS. 1-8, the conductive fiber brush 21 is arranged to the housing 10, and in the radial direction of the housing 10, the conductive fiber brush 21 gradually extends away from an axis of the housing 10. That is, a tip of the conductive fiber brush 21 protrudes from an outer circumferential face of the housing 10. Thus, it facilitates better and more convenient cleaning of the tip of the conductive fiber brush 21 by a subsequent cleaning member 32.

It could be understood that the cleaning member 32 may sweep over the conductive fiber brush 21 to clean the conductive fiber brush 21.

Figure 2:
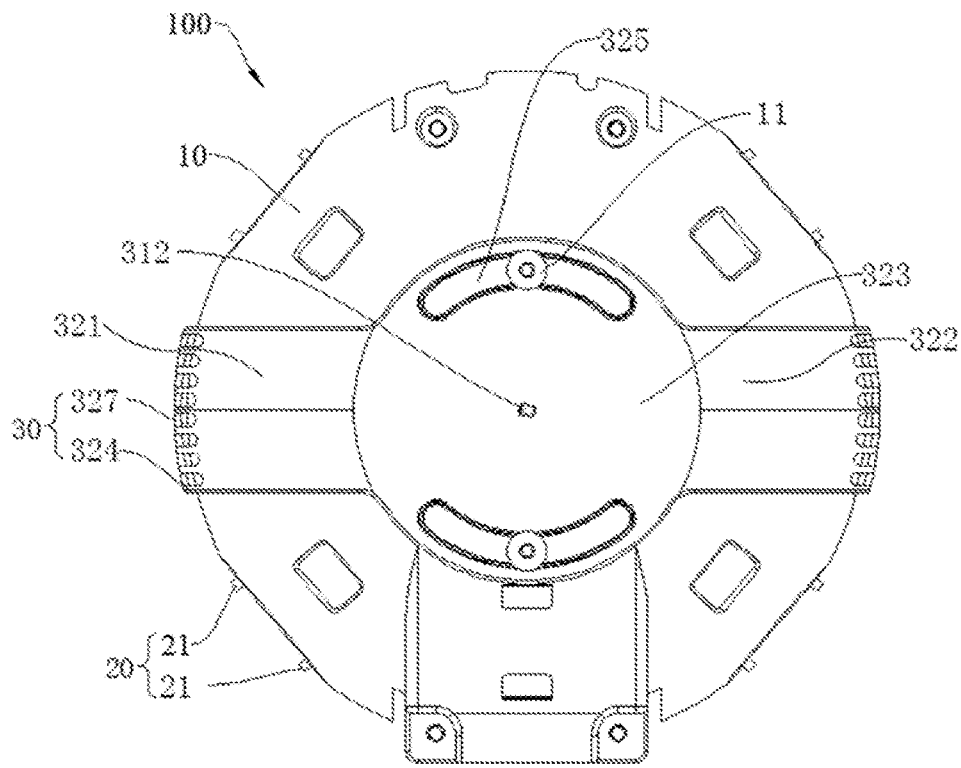
FIG. 2 is a top view of the negative ion generating device in FIG. 1.

In the present disclosure, as illustrated in FIGS. 1-2, the cleaning member 32 is rotatably arranged to the housing 10. In a horizontal direction, the cleaning member 32 and the tip of the conductive fiber brush 21 are substantially located at the same horizontal position, and the cleaning member 32 may rotate freely in a horizontal plane around its axial direction. During rotation of the cleaning member 32, the cleaning member 32 may come into contact with the tip of the conductive fiber brush 21.

It could be understood that, in the present disclosure, the cleaning member 32 may come into contact with the tip of the conductive fiber brush 21, and friction occurs between the cleaning member 32 and the conductive fiber brush 21, thus, the cleaning member 32 may clean up debris on a surface of the conductive fiber brush 21.

The technical solution provided by embodiments of the present disclosure may have the following beneficial effects: the cleaning member 32 which may rotate freely is arranged on the housing 10, the cleaning member 32 may sweep over the conductive fiber brush 21 periodically, and the cleaning member 32 can clean up debris adsorbed on the conductive fiber brush 21, achieving cleaning of the conductive fiber brush 21, solving a risk of blocking of the conductive fiber brush 21 and improving service life of the conductive fiber brush 21.

In some embodiments, the conductive fiber brush 21 is arranged along a circumferential edge of the housing 10; and the cleaning member 32 can rotate clockwise and/or counterclockwise around an edge of the housing 10 in a horizontal direction under action of the power provided by the driving mechanism 31, and contact and separate from the conductive fiber brush 21 during rotation.

Specifically, as illustrated in FIG. 2, in the horizontal direction, the tip of the conductive fiber brush 21 protrudes from an outer circumferential face of the housing 10, and the cleaning member 32 substantially rotates along the outer circumferential face of the housing 10. Thus, the cleaning member may realize cleaning operation of the tip of the conductive fiber brush 21.

In some embodiments, the conductive fiber brush 21 employs elastic material, the conductive fiber brush 21 is elastically deformed during contact with the cleaning member 32; and the conductive fiber brush 21 relies on its own elasticity to restore its shape after separation from the cleaning member 32.

It could be understood that, the conductive fiber brush 21 is made of elastic material, and the conductive fiber brush 21 may perform elastic deformation, effectively prolonging the service life of the conductive fiber brush 21.

Figure 3:
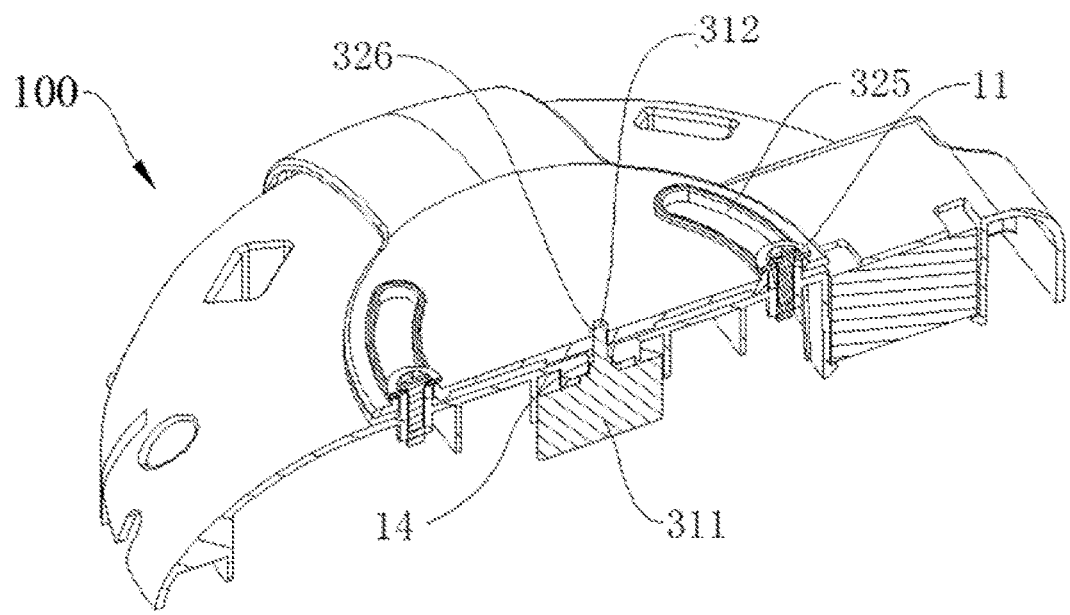
FIG. 3 is a sectional view of the negative ion generating device in FIG. 1.
Figure 4:
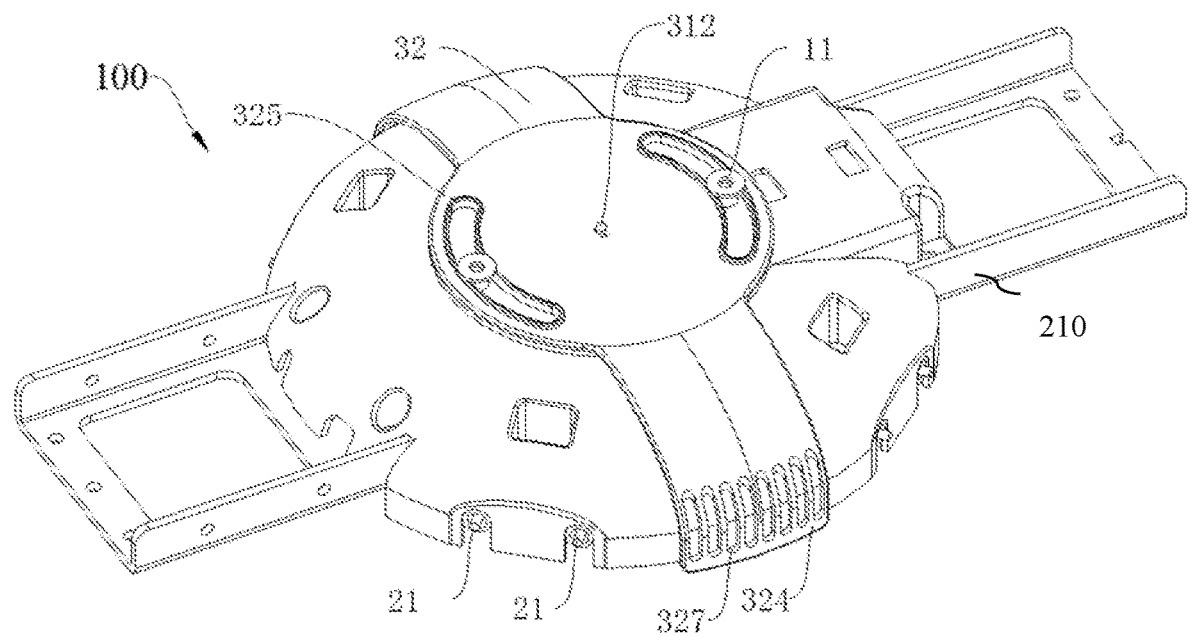
FIG. 4 is another perspective view of a negative ion generating device illustrated according to one or more examples of the present disclosure.

In the present disclosure, FIG. 3 is a sectional view of a negative ion generating device illustrated according to an exemplary embodiment. FIG. 4 is another perspective view of a negative ion generating device illustrated according to an exemplary embodiment.

In some embodiments, as illustrated in FIGS. 1-8, the cleaning member 32 includes a rotation coupling part 323, a first cantilever 321 and a second cantilever 322. The rotation coupling part 323 is arranged at an upper surface of the housing 10, and the rotation coupling part 323 is rotatably coupled to the housing 10. The first cantilever 321 and the second cantilever 322 are symmetrically arranged at two opposite ends of the rotation coupling part 323, each of the first cantilever 321 and the second cantilever 322 has a first end coupled to the rotation coupling part 323 and a second end provided with a cleaning part 324, and the cleaning part 324 can contact or separate from the conductive fiber brush 21 during rotation.

Specifically, in the present disclosure, the cleaning member 32 includes a rotation coupling part 323, a first cantilever 321 and a second cantilever 322. The rotation coupling part 323 has a substantially disc-shaped structure, and the first cantilever 321 and the second cantilever 322 are symmetrically arranged at two sides of the rotation coupling part 323 with respect to an axis of the rotation coupling part 323.

In the present disclosure, each of an extending end of the first cantilever 321 and an extending end of the second cantilever 322 is provided with the cleaning part 324. In the horizontal direction, the cleaning part 324 and the tip of the conductive fiber brush 21 are substantially located at the same horizontal position, and the cleaning part 324 may rotate freely in the horizontal plane around an axial direction of the rotation coupling part 324. During rotation of the cleaning part 324, the cleaning part 324 may come into contact with or separate from the tip of the conductive fiber brush 21. Friction occurs between the cleaning part 324 and the conductive fiber brush 21, thus, the cleaning part 324 may clean up debris on a surface of the conductive fiber brush 21.

In some embodiments, as illustrated in FIGS. 1-8, the upper surface of the housing 10 is fixed with a limiting post 11; the rotation coupling part 323 defines a limiting hole 325; and the limiting hole 325 can fit over the limiting post 11 and cooperate with the limiting post 11 to achieve limit of the cleaning part 324 in a rotation state.

It could be understood that, in the present disclosure, the outer circumferential face of the housing 10 is not a regular hemisphere, and the outer circumferential face of the housing 10 may be further provided with a coupling member, a fixing member and other components.

Therefore, the cleaning member 32 is generally not set to have a circular rotation of 360° on the housing, but is set to have a reciprocating rotation within a certain rotation range.

In the present disclosure, as illustrated in FIGS. 1-4, the cleaning member 32 defines a limiting hole 325, and a top of the housing 10 is provided with a limiting post 11. During rotation of the cleaning member 32, the limiting post 11 is always located in the limiting hole 325. Thus, the rotation range of the cleaning member 32 may be defined by setting an arc length of the limiting hole 325.

In the present disclosure, the cleaning member 32 defines the limiting hole 325, the housing 10 is provided with the limiting post 11, the rotation range of the cleaning member 32 on the housing 10 is effectively defined, facilitating prevention of collision of the cleaning member 32 with other components on the housing 10 (e.g., the outer circumferential face of the housing 10 may be further provided with a coupling member and a fixing member), and effectively improving safety and rationality of an overall structure of the negative ion generating device 100.

In some other embodiments, the limiting post 11 may also be configured as a bolt. It could be understood that, the top of the housing 10 may define a threaded hole, the cleaning member 32 is firstly arranged on the housing 10, and then the bolt is fixed in the threaded hole of the housing 10.

A top of the bolt has a cap, and the cap has a diameter greater than a width of the limiting hole 325. Thus, the bolt may be used to prevent the cleaning member 32 from separating from the housing 10, effectively improving the safety of the cleaning member 32 during rotation.

In some embodiments, as illustrated in FIGS. 1-4, two limiting holes 325 are provided, two limiting posts 11 are provided; and the two limiting holes 325 are symmetrically arranged at two sides of a center of the rotation coupling part 323.

It could be understood that, the rotation coupling part 323 has a substantially circular plate structure, and the two limiting holes 325 are symmetrically arranged at two sides of the center of the rotation coupling part 323, effectively improving the stability of the rotation coupling part 323 during the rotation.

In some embodiments, as illustrated in FIGS. 1-8, the upper surface of the housing 10 has a curvature with a high center and a low edge; each of the first cantilever 321 and the second cantilever 322 has a curved plate shape matching the curvature of the upper surface of the housing 10; and the limiting hole 325 has a curved shape.

Figure 6:
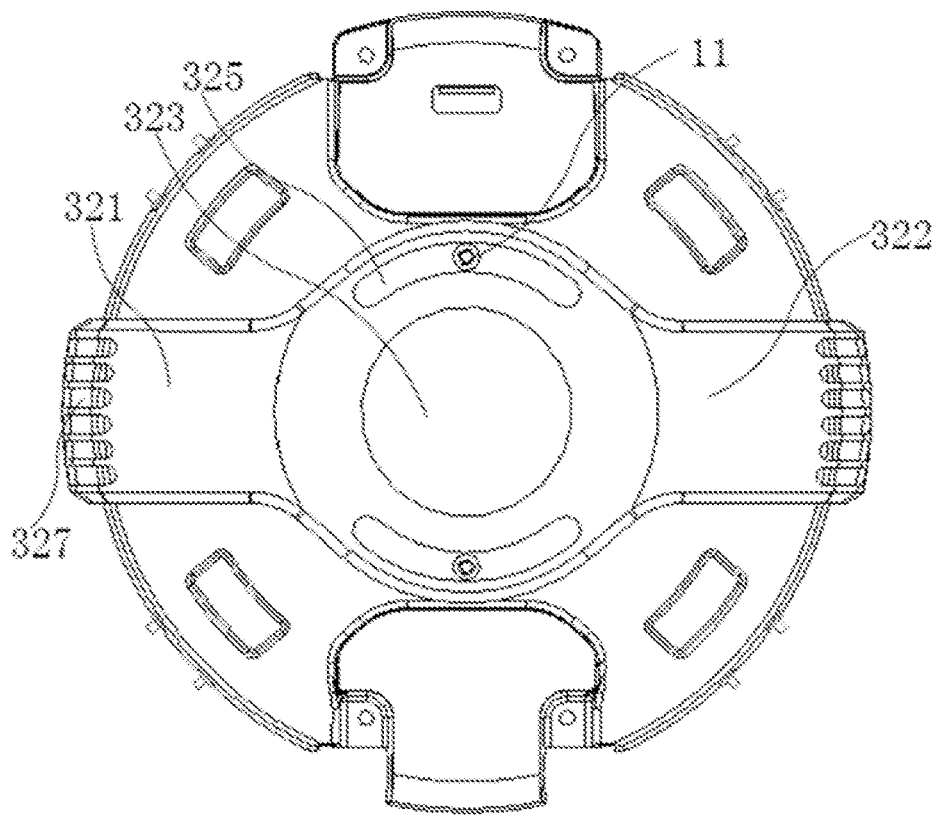
FIG. 6 is still another perspective view of a negative ion generating device illustrated according to one or more examples of the present disclosure.
Figure 7:
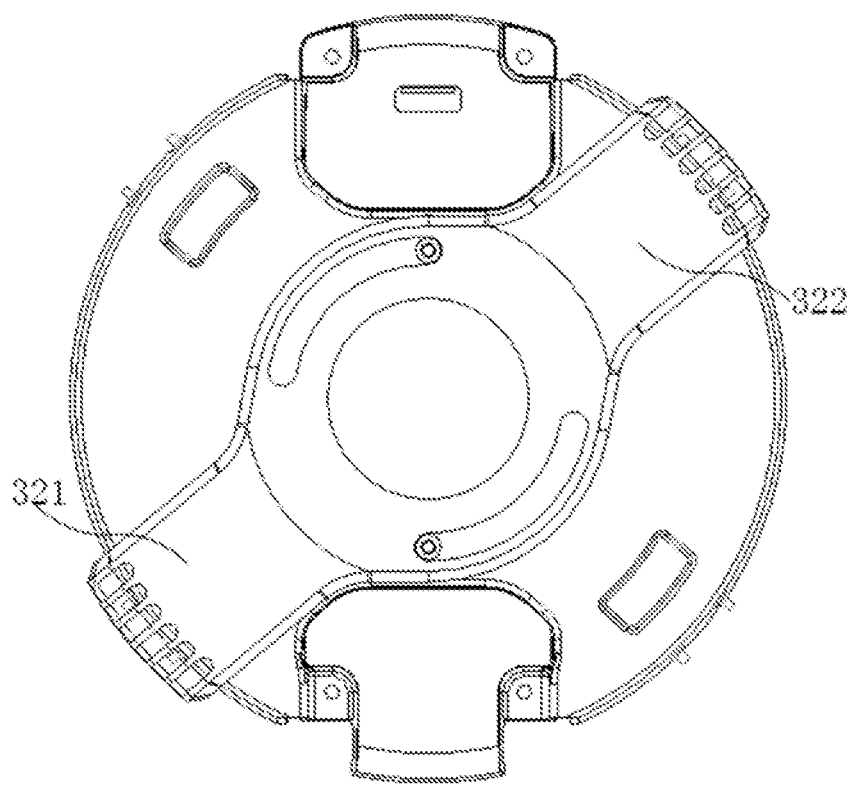
FIG. 7 is a schematic view of the negative ion generating device in FIG. 6 in a first rotation position.
Figure 8:
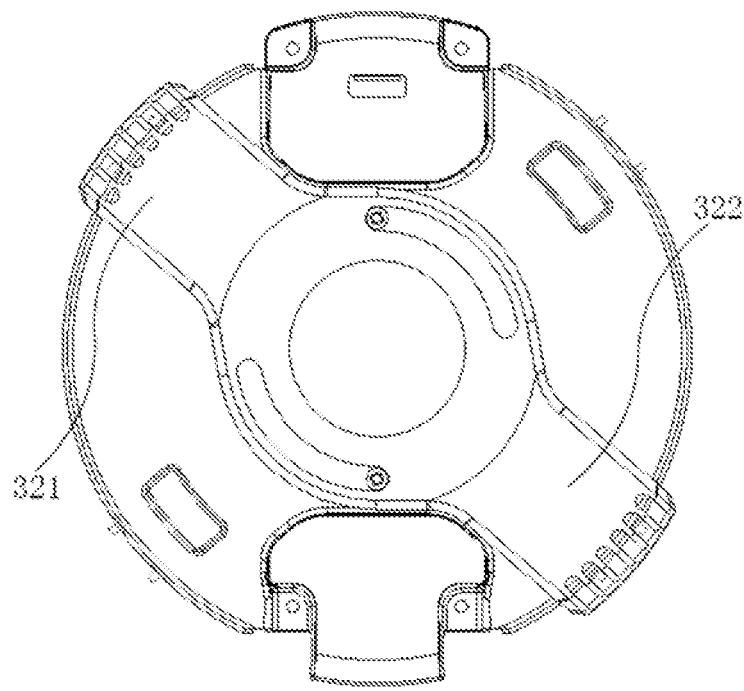
FIG. 8 is a schematic view of the negative ion generating device in FIG. 6 in a second rotation position.

FIG. 6 is a perspective view of a negative ion generating device illustrated according to one or more examples of the present disclosure. FIG. 7 is a schematic view of the negative ion generating device in FIG. 6 in a first rotation position. FIG. 8 is a schematic view of the negative ion generating device in FIG. 6 in a second rotation position. It could be understood that, as illustrated in FIGS. 6 to 8, the first cantilever 321 and the second cantilever 322 may rotate around the axis of the housing 10, and thus rotational track of the first cantilever 321 and the second cantilever 322 is a circular arc. Therefore, the first cantilever 321 and the second cantilever 322 perform an arc-shaped movement on the housing 10, and the upper surface of the housing 10 has the curvature with the high center and the low edge, such that movement process of the first cantilever 321 and the second cantilever 322 is more convenient and reasonable.

In the present disclosure, the limiting hole 325 has a curved shape, such that the limiting hole 325 matches the rotational track of the first cantilever 321 and the second cantilever 322.

In some embodiments, as illustrated in FIGS. 1-8, the cleaning member 32 takes a center of the rotation coupling part 323 as a center of rotation, and is configured to rotate clockwise or counterclockwise under action of the driving mechanism 31.

It could be understood that under the action of the driving mechanism 31, the cleaning member 32 takes the center of the rotation coupling part 323 as the center of rotation, and the cleaning member 32 perform reciprocating rotation on the housing 10.

In some embodiments, as illustrated in FIGS. 1-8, an axis where a center of the cleaning member 32 is located coincides with an axis where a center of the housing is located.

In the present disclosure, the cleaning member 32 is rotatably arranged to the housing 10, and the axis of the cleaning member 32 and the axis of the housing 10 are located in the same straight line.

In some other embodiments of the present disclosure, the housing 10 may be configured to have a hemispherical shape, the cleaning member 32 may have a circular arc shape, the cleaning member 32 is arranged on a spherical face of the housing 10, and the axis of the cleaning member 32 and the axis of the housing 10 are located in the same straight line. Thus, friction of the cleaning member 32 and the housing 10 during the rotation of the cleaning member 32 is effectively reduced, abrasion between the cleaning member 32 and the housing 10 is reduced, and prolonging of the service life of the cleaning member 32 and the housing 10 is facilitated.

In the present disclosure, as illustrated in FIGS. 1-4, the housing 10 has a substantially hemispherical shape, and therefore, a circumferential area of the housing 10 is larger as it is closer to a bottom of the housing 10. The conductive fiber brush 21 is arranged at the bottom of the housing 10, facilitating better setting of number and position of the conductive fiber brushes 21 and improving utilization efficiency of the housing 10.

In the present disclosure, as illustrated in FIGS. 1-4, the conductive fiber brush 21 is arranged at the bottom of the housing 10, and correspondingly, the cleaning part 324 is arranged at an end part of the cleaning member 32.

In some embodiments, as illustrated in FIGS. 1-4, a distance between the axis where the center of the housing 10 is located and a tip of the conductive fiber brush 21 is a first distance; a distance between the axis where the center of the housing 10 is located and the cleaning part 324 is a second distance; and the first distance is greater than the second distance.

Specifically, as illustrated in FIGS. 1-4, in the radial direction of the housing 10, the distance between the tip of the conductive fiber brush 21 and the axis of the housing 10 is greater than the distance between the cleaning part 324 and the axis of the housing 10.

In the present disclosure, in the radial direction of the housing 10, the conductive fiber brush 21 gradually extends away from the axis of the housing 10, and there is a first distance between the tip of the conductive fiber brush 21 and the axis of the housing 10.

In the present disclosure, the cleaning part 324 may rotate freely around the axis of the housing 10, and thus, relative distance between the cleaning part 324 and the axis of the housing 10 does not change.

In the present disclosure, relative distance between the cleaning part 324 and the axis of the housing 10 is less than the distance between the tip of the conductive fiber brush 21 and the axis of the housing 10. That is, a rotational track of the cleaning part 324 is located inside a circumferential track surrounding by tips of a plurality of conductive fiber brushes 21. Thus, during the rotation of the cleaning part 324, the cleaning part 324 can better contact and rub the tip of the conductive fiber brush 21, facilitating improvement of the cleaning effect of the cleaning part 324.

In some embodiments, the negative ion assembly 20 further includes a negative ion circuit board 40 electrically coupled to the conductive fiber brush 21; and the negative ion circuit board 40 is fixed to a lower surface or an inner cavity of the housing 10.

Specifically, the housing 10 defines an inner cavity, the negative ion circuit board 40 is arranged in the inner cavity, and the conductive fiber brush 21 is electrically coupled to the negative ion circuit board 40. Thus, the housing 10 may be used to protect the negative ion circuit board 40. Meanwhile, the housing 10 provides good operational environment for the negative ion circuit board 40, prevents outside dust from adsorbing on the negative ion circuit board 40, and improves the safety of the negative ion circuit board 40.

In some embodiments, the circumferential edge of the housing 10 is provided with a protruding rib 12 protruding from the lower surface; the protruding rib 12 defines a brush through hole 13 or a brush groove (not illustrated); and the conductive fiber brush 21 is inserted into the brush through hole 13 or the brush groove.

In the present disclosure, as illustrated in FIGS. 1, 2, and 3, the conductive fiber brush 21 has at least a portion arranged in the inner cavity of the housing 10. The at least a portion of the conductive fiber brush 21 is coupled to the negative ion circuit board 40, and the negative ion circuit board 40 may transit a Dc negative high voltage current to the conductive fiber brush 21.

In the present disclosure, as illustrated in FIGS. 1, 2, and 3, the conductive fiber brush 21 has at least another portion passing through the brush through hole 13 and extending from the housing 10, and a portion thereof located outside the housing 10 is the tip of the conductive fiber brush 21.

In the present disclosure, a diameter of the brush through hole 13 is slightly greater than a diameter of the conductive fiber brush 21. Thus, in the process of the cleaning part 324 on the cleaning member 32 cleaning the tip of the conductive fiber brush 21, the brush through hole 13 facilitates improvement of the stability of the conductive fiber brush 21, and reduces amplitude of left and right shaking.

In some embodiments, as illustrated in FIGS. 1-4, a plurality of brush through holes 13 or brush grooves are provided. The number of the conductive fiber brushes 21 matches with the brush through holes 13 or the brush grooves; the plurality of brush through holes 13 or the plurality of brush grooves are spaced apart in a circumferential direction of the housing 10; and a plurality of conductive fiber brushes 21 correspond to the plurality of brush through holes 13 or the plurality of brush grooves in arrangement position.

In the present disclosure, as illustrated in FIGS. 1-4, the housing 10 may define a plurality of brush through holes 13, the plurality of brush through holes are spaced apart along the circumferential direction of the housing 10, and each brush through hole 13 may be internally provided with one conductive fiber brush 21. Thus, improvement of operational efficiency of the negative ion generating device 100 is facilitated.

In the present disclosure, the plurality of brush through holes 13 may be evenly spaced apart in the circumferential direction of the housing 10. In the present disclosure, the plurality of brush through holes 13 may be divided into a plurality of groups, and the plurality of groups of brush through holes 13 may be evenly spaced apart in the circumferential direction of the housing 10. However, the present disclosure is not limited to this. The plurality of brush through holes 13 may also be unequally spaced apart.

In the present disclosure, in a vertical direction, the plurality of brush through holes 13 may be divided into a plurality of layers. Thus, space utilization of the housing 10 is further improved, arrangement of more conductive fiber brushes 21 is facilitated, and operational efficiency of the negative ion generating device 100 is further improved.

Figure 5:
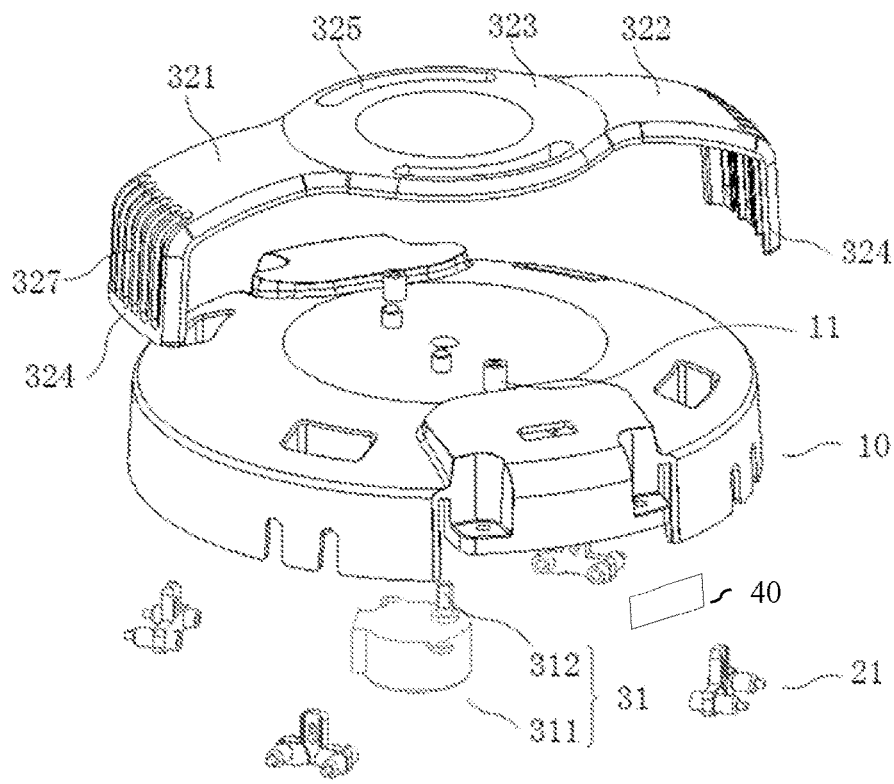
FIG. 5 is an exploded view of a negative ion generating device illustrated according to one or more examples of the present disclosure.

FIG. 5 is an exploded view of a negative ion generating device illustrated according to one or more examples of the present disclosure. In some embodiments illustrated in FIG. 5, the driving mechanism 31 includes a motor 311, and the motor 311 has a rotating shaft 312. A center of the housing 10 defines a first motor through hole 14; and a center of the cleaning member 32 defines a second motor through hole 326. The motor 311 is fixed to the housing 10, the rotating shaft 312 passes through the first motor through hole 14 and the second motor through hole 326 and is fixedly coupled to the cleaning member 32, to drive the cleaning member 32 to rotate synchronously.

In the present disclosure, the driving mechanism 31 further includes a motor 311 and a rotating shaft 312 coupled to each other, the motor 311 is arranged in the inner cavity of the housing 10, the rotating shaft 312 passes through the housing 10, an axis of the rotating shaft coincides with the axis of the housing 10, and the cleaning member 32 is fitted over the rotating shaft 312 to rotate with the rotating shaft 312.

Specifically, a center of the housing 10 defines a first motor through hole 14; and a center of the cleaning member 32 defines a second motor through hole 326. The rotating shaft 312 passes through the first motor through hole 14 and the second motor through hole 326 and is fixedly coupled to the cleaning member 32, to drive the cleaning member 32 to rotate synchronously.

In the present disclosure, as illustrated in FIG. 3, the motor 311 is arranged in the housing 10. Thus, the housing 10 may be used to protect and fix the motor 311, facilitating the stability of the motor 311.

In the present disclosure, as illustrated in FIG. 3, a lower end of the rotating shaft 312 is coupled to the motor 311, and the motor 311 may drive the rotating shaft 312 to rotate freely. The cleaning member 32 is arranged on the rotating shaft 312. Thus, the rotating shaft 32 may drive the cleaning member 32 to rotate around the housing 10, to render the cleaning part 324 to clean the tip of the conductive fiber brush 21.

It could be understood that in the present disclosure, the axis of the housing 10, the axis of the rotating shaft 312 and the axis of the cleaning member 32 are located in the same straight line.

In some embodiments, the cleaning member 32 defines a through hole 327 or a notch at a position corresponding to the conductive fiber brush 21.

In some embodiments, the through hole 327 has a size greater than an outer diameter of the conductive fiber brush 21.

In the present disclosure, the cleaning part 324 defines the through hole 327, and in the horizontal direction, the through hole 327 and the tip of the conductive fiber brush 21 are located in the same horizontal plane.

The size of the through hole 327 is greater than the outer diameter of the conductive fiber brush 21. Thus, after the tip of the conductive fiber brush 21 contacts the through hole 327, the tip of the conductive fiber brush 21 may extend into the through hole 327, the through hole 327 may have a sufficient contact with the outer circumferential face of the conductive fiber brush 21, facilitating better cleaning of adsorbate on the surface of the conductive fiber brush 21 by the through hole 327.

In some other embodiments of the present disclosure, the cleaning part 324 defines a notch (not illustrated), the notch passes through an upper surface and a lower surface of the cleaning member 32, and an opening of the notch is oriented towards an end away from the center of rotation.

It could be understood that, an area of the notch is generally greater than an area of the through hole 327. Thus, the tip of the conductive fiber brush 21 may extend into the notch more quickly, facilitating cleaning efficiency and cleaning quality of the cleaning part 324.

In some embodiments, as illustrated in FIGS. 1-4, a plurality of through holes 327 are provided, and the plurality of through holes 327 are arranged at the cleaning part 324 side by side.

In the present disclosure, as illustrated in FIGS. 1-4, the cleaning part 324 defines a plurality of through holes 327 arranged side by side. Thus, the plurality of through holes 327 may clean the conductive fiber brush 21 sequentially, effectively improving the cleaning efficiency and cleaning effect of the cleaning part 324.

Figure 9:
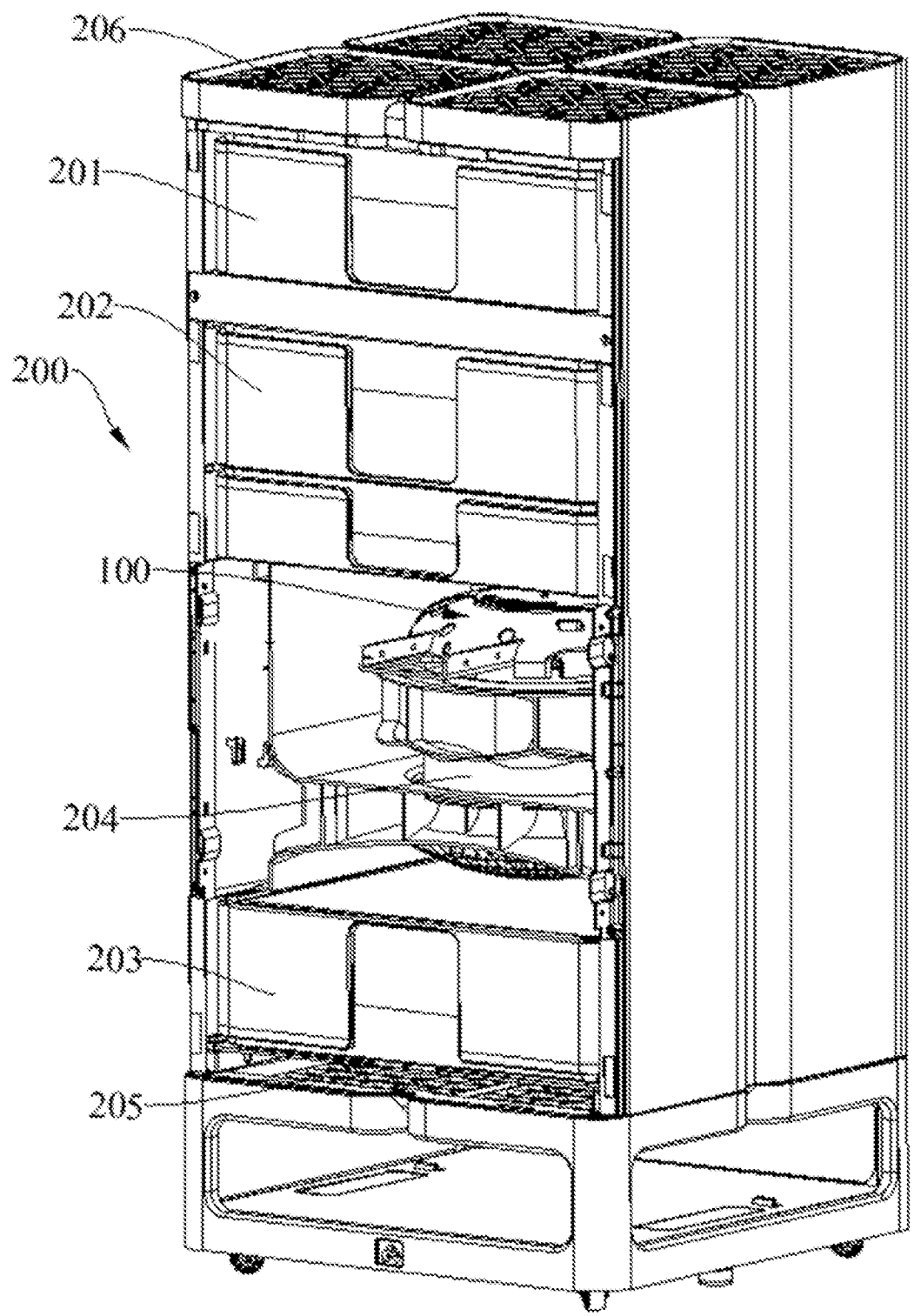
FIG. 9 is a perspective view of an air purifier illustrated according to one or more examples of the present disclosure.

FIG. 9 is a perspective view of an air purifier illustrated according to an exemplary embodiment.

As illustrated in FIG. 3, according to a second aspect of embodiments of the present disclosure, an air purifier 200 is provided, which includes a negative ion generating device 100 according to any embodiment in the present disclosure.

In some embodiments, the negative ion generating device 100 is fixed in the air purifier 200 with a screw or snap connection.

In the present disclosure, as illustrated in FIGS. 4 and 9, the housing 10 of the negative ion generating device 100 may also be provided with a bracket 210. The bracket 210 is arranged below the housing 10, and two ends of the cleaning member 32 are arranged at two sides of the bracket 210. The cleaning member 32 defines the limiting hole 325 and the housing 10 is provided with the limiting post 11 to effectively define the rotation range of the cleaning member 32, such that the cleaning member 32 will not collide with the bracket 210 during the rotation.

In the present disclosure, as illustrated in FIG. 9, the bracket 210 may be provided with a plurality of connection holes, the negative ion generating device 100 may be fixed in the air purifier 200 by the bracket 210, and the bracket 210 facilitates improvement of convenience during mounting and detachment of the negative ion generating device 100.

In some other embodiments, the negative ion generating device 100 may also be directly coupled in the air purifier 200 through the housing 10.

In some embodiments, the air purifier 200 is provided with a fan 204, the fan 204 is rotatable to form a wind path in the air purifier 200, and the negative ion generating device 100 is arranged in the wind path or outside the wind path.

In the present disclosure, as illustrated in FIG. 9, the air purifier 200 is provided with a first filter cartridge 201, a second filter cartridge 202, a third filter cartridge 203, and a fan 204.

A bottom of the air purifier 200 defines an air inlet 205, and a top of the air purifier 200 defines an air outlet 206.

The first filter cartridge 201 is a high efficiency filter cartridge, the second filter cartridge 202 is a medium efficiency filter cartridge, and the third filter cartridge 203 is a primary filter cartridge.

The fan 204 rotates to produce wind pressure, filter cartridges having different purifying efficiency such as the first filter cartridge 201, the second filter cartridge 202 and the third 203 are arranged at an air inlet side or an air outlet side of the fan 204.

It could be understood that, in the present disclosure, the arrangement position and number of the first filter cartridge 201, and the second filter cartridge 202 and the third filter cartridge 203 can be adjusted according to actual needs, and the arrangement type of the first filter cartridge 201, and the second filter cartridge 202 and the third filter cartridge 203 can be adjusted according to actual needs.

In the present disclosure, as illustrated in FIG. 9, the air outlet 206 and the air inlet 205 are generally formed by a perforated structural member or a grille, the air inlet 205 is generally arranged at a bottom of the air purifier 200 or at front, rear, left and right sides, and the arrangement position and size of the air inlet 205 may be adjusted according to actual needs.

The negative ion generating device 100 is generally arranged in the wind path formed by rotation of the fan 204, the negative ion generating device 100 may be arranged in front of or behind the fan 204, and the negative ion generating device 100 may also be arranged between the fan 204 and the filter cartridges or between filter cartridges.

In the present disclosure, the negative ion generating device 100 may also be arranged between the air inlet 205 and the filter cartridges, between the air outlet 206 and the filter cartridges, between the air outlet 206 and the fan 204 or between the air outlet 206 and the fan 204.

In some other embodiments, the negative ion generating device 100 may also be arranged at a side face outside the wind path.

In the present disclosure, as illustrated in FIG. 9, the negative ion generating device 100 is coupled to other apparatuses in the air purifier 200 through the bracket 210, and the negative ion generating device 100 is fixed in the air purifier 200 by a screw or snap connection.

In some other embodiments, the negative ion generating device 100 may also be directly provided with a snap or screw hole for connection, such that the negative ion generating device 100 is coupled to the other apparatuses in the air purifier 200.

It could be understood that in the present disclosure, "plurality of" refers to two or more than two, and other quantifiers are similar. The term "and/or", describes the association relationship of the associated objects, and means that there can be three types of relationships. For example, A and/or B, can mean that A exists alone, A and B exist at the same time, and B exists alone. The character "/" generally indicates that the associated objects before and after it are an "or" relationship. The singular form "a", "the" and "this" is also intended to include the plural form, unless other meanings are explicitly expressed in the context.

It should be further understood that, although the terms "first", "second" may be employed to describe various information, these information should not limited by these terms. These terms are only used to distinguish the information of the same type from each other, and do not indicate special order or importance. In fact, the expressions "first", "second", etc. are completely interchangeable. For example, a first information may be referred to as a second information without departing from the scope of the present disclosure, and similarly, the second information may also be referred to as the first information.

It could be further understood that terms such as "central," "longitudinal," "transverse," "front," "rear," "upper," "lower," "left," "right," "vertical," "horizontal," "top," "bottom," "inner," "outer," should be construed to refer to the orientation as then described or as shown in the drawings under discussion. These relative terms are for convenience of description of the embodiments and simplification of the description and do not require that the indicated or suggested devices or element must be constructed or operated in a particular orientation.

It could be further understood that, unless otherwise specified, "connection" includes a direct connection between the two without other components, and also includes an indirect connection between the two with other elements.

It could be further understood that, although the operations in embodiments of the present disclosure are described in a specific order in the drawings, it should not be construed as requiring that the operations be performed in the specific order shown or the serial order, or requiring that all operations shown be performed to obtain the desired result. In certain circumstances, multitasking and parallel processing may be advantageous.

Other embodiments of the present disclosure will readily occur to a person skilled in the art upon consideration of the specification and practice of the invention disclosed herein. The present application is intended to cover any variations, uses, or adaptations of the present disclosure that follow the general principles of the present disclosure and include common knowledge or conventional technical means in the art not disclosed by the present disclosure. The specification and embodiments are to be regarded as exemplary only, with the true scope and spirit of the disclosure being indicated by the following claims.

It should be understood that the present disclosure is not limited to the precise structures described above and illustrated in the accompanying drawings, and that various modifications and changes may be made without departing from the scope thereof. The scope of the present disclosure is limited only by the scope of the appended claims.

In order to overcome problems existing in the related art, the present disclosure provide a negative ion generating device and an air purifier.

According to a first aspect of embodiments of the present disclosure, a negative ion generating device is provided, which includes a housing; a negative ion assembly arranged to the housing, the negative ion assembly being configured to produce a negative ion, the negative ion assembly including a conductive fiber brush; and a cleaning assembly arranged to the housing, the cleaning assembly including a driving mechanism and a cleaning member coupled to a power output end of the driving mechanism, the driving mechanism being configured to provide power, the cleaning member being capable of moving under action of the power provided by the driving mechanism, and contacting or separating from the conductive fiber brush during movement.

In some embodiments, the conductive fiber brush is arranged along a circumferential edge of the housing; and the cleaning member is capable of rotating clockwise and/or counterclockwise around an edge of the housing in a horizontal direction under action of the power provided by the driving mechanism, and contacting and separating from the conductive fiber brush during rotation.

In some embodiments, the conductive fiber brush employs elastic material: the conductive fiber brush is elastically deformed during contact with the cleaning member; and the conductive fiber brush relies on its own elasticity to restore its shape after separation from the cleaning member.

In some embodiments, the cleaning member include a rotation coupling part, a first cantilever and a second cantilever; the rotation coupling part is arranged at an upper surface of the housing and rotatably coupled to the housing; the first cantilever and the second cantilever are symmetrically arranged at two opposite ends of the rotation coupling part; each of the first cantilever and the second cantilever has a first end coupled to the rotation coupling part and a second end provided with a cleaning part capable of contacting or separating from the conductive fiber brush during rotation.

In some embodiments, the upper surface of the housing is fixed with a limiting post; the rotation coupling part defines a limiting hole; and the limiting hole is capable of fitting over the limiting post and cooperating with the limiting post to achieve limit of the cleaning part in a rotation state.

In some embodiments, two limiting holes are provided, two limiting posts are provided; and the two limiting holes are symmetrically arranged at two sides of a center of the rotation coupling part.

In some embodiments, the upper surface of the housing has a curvature with a high center and a low edge; each of the first cantilever and the second cantilever has a curved plate shape matching the curvature of the upper surface of the housing; and In some embodiments, the cleaning member takes a center of the rotation coupling part as a center of rotation, and is configured to rotate clockwise or counterclockwise under action of the driving mechanism.

In some embodiments, an axis where a center of the cleaning member is located coincides with an axis where a center of the housing is located.

In some embodiments, a distance between the axis where the center of the housing is located and a tip of the conductive fiber brush is a first distance; a distance between the axis where the center of the housing is located and the cleaning part is a second distance; and the first distance is greater than the second distance.

In some embodiments, the negative ion assembly further includes a negative ion circuit board electrically coupled to the conductive fiber brush; and the negative ion circuit board is fixed to a lower surface or an inner cavity of the housing.

In some embodiments, the circumferential edge of the housing is provided with a protruding rib protruding from the lower surface; the protruding rib defines a brush through hole or a brush groove; and the conductive fiber brush is inserted into the brush through hole or the brush groove.

In some embodiments, a plurality of brush through holes or brush grooves are provided; a number of the conductive fiber brushes matches with the brush through holes or the brush grooves; the plurality of brush through holes or the plurality of brush grooves are spaced apart in a circumferential direction of the housing; and a plurality of conductive fiber brushes correspond to the plurality of brush through holes or the plurality of brush grooves in arrangement position.

In some embodiments, the driving mechanism includes a motor having a rotating shaft; a center of the housing defines a first motor through hole; a center of the cleaning member defines a second motor through hole, the motor is fixed to the housing; and the rotating shaft passes through the first motor through hole and the motor through hole sequentially to fixedly couple to the cleaning member, to drive the cleaning member to rotate synchronously.

In some embodiments, the cleaning member defines a through hole or a notch at a position corresponding to the conductive fiber brush.

In some embodiments, the through hole has a size greater than an outer diameter of the conductive fiber brush.

In some embodiments, a plurality of through holes are provided, and the plurality of through holes are arranged side by side and spaced apart.

According to a second aspect of embodiments of the present disclosure, an air purifier is provided, which includes a negative ion generating device according to any embodiment in the present disclosure.

In some embodiments, the air purifier is provided with a fan, the fan is rotatable to form a wind path in the air purifier, and the negative ion generating device is arranged in the wind path or outside the wind path.

In some embodiments, the negative ion generating device is fixed in the air purifier with a screw or snap connection.

The technical solution provided by embodiments of the present disclosure may have the following beneficial effects: the cleaning member which may rotate freely is arranged on the housing, the cleaning member may sweep over the conductive fiber brush periodically, and the cleaning member can clean up debris adsorbed on the conductive fiber brush, achieving cleaning of the conductive fiber brush, solving a risk of blocking of the conductive fiber brush and improving service life of the conductive fiber brush.

What is claimed is:
1. A negative ion generating device, comprising:
a housing;
a negative ion assembly disposed in the housing, the negative ion assembly being configured to produce a negative ion, the negative ion assembly comprising a conductive fiber brush; and
a cleaning assembly disposed in the housing, the cleaning assembly comprising a driving mechanism and a cleaning member coupled to a power output end of the driving mechanism, the driving mechanism being configured to provide power, the cleaning member being configured to move under action of the power provided by the driving mechanism, and contact or separate from the conductive fiber brush during movement,
wherein the conductive fiber brush is disposed along a circumferential edge of the housing; and
the cleaning member is configured to rotate clockwise or counterclockwise around an edge of the housing in a horizontal direction under action of the power provided by the driving mechanism, and contact and separate from the conductive fiber brush during rotation.
2. The negative ion generating device according to claim 1, wherein
the conductive fiber brush is made of an elastic material:
the conductive fiber brush is elastically deformed during contact with the cleaning member; and the conductive fiber brush restores to an original shape due to elasticity after separation from the cleaning member.

3. The negative ion generating device according to claim 1, wherein
the cleaning member comprises a rotation coupling part, a first cantilever and a second cantilever;
the rotation coupling part is arranged at an upper surface of the housing and rotatably coupled to the housing;
the first cantilever and the second cantilever are symmetrically arranged at two opposite ends of the rotation coupling part; and
each of the first cantilever and the second cantilever comprises a first end coupled to the rotation coupling part and a second end provided with a cleaning part capable of contacting or separating from the conductive fiber brush during rotation.

4. The negative ion generating device according to claim 3, wherein
the upper surface of the housing comprises a limiting post, and the limiting post is fixedly attached on the upper surface of the housing;
the rotation coupling part defines a limiting hole; and
the limiting hole is configured to fit over the limiting post and cooperate with the limiting post to achieve limit of the cleaning part in a rotation state.

5. The negative ion generating device according to claim 4, wherein
two limiting holes are provided, two limiting posts are provided; and
the two limiting holes are symmetrically arranged at two sides of a center of the rotation coupling part.

6. The negative ion generating device according to claim 4, wherein
the upper surface of the housing has a curvature with a high center and a low edge;
each of the first cantilever and the second cantilever has a curved plate shape matching the curvature of the upper surface of the housing; and
the limiting hole has a curved shape.

7. The negative ion generating device according to claim 3, wherein
the cleaning member takes a center of the rotation coupling part as a center of rotation, and is configured to rotate clockwise or counterclockwise under action of the driving mechanism.

8. The negative ion generating device according to claim 7, wherein
an axis where a center of the cleaning member is located coincides with an axis where a center of the housing is located.

9. The negative ion generating device according to claim 8, wherein
a distance between the axis where the center of the housing is located and a tip of the conductive fiber brush is a first distance;
a distance between the axis where the center of the housing is located and the cleaning part is a second distance; and
the first distance is greater than the second distance.

10. The negative ion generating device according to claim 1, wherein
the negative ion assembly further comprises a negative ion circuit board electrically coupled to the conductive fiber brush; and
the negative ion circuit board is fixed to a lower surface or an inner cavity of the housing.

11. The negative ion generating device according to claim 10, wherein
a circumferential edge of the housing is provided with a protruding rib protruding from the lower surface;
the protruding rib defines a brush through hole or a brush groove; and
the conductive fiber brush is inserted into the brush through hole or the brush groove.

12. The negative ion generating device according to claim 11, wherein
a plurality of brush through holes or brush grooves are provided;
a number of the conductive fiber brushes matches the brush through holes or the brush grooves;
the plurality of brush through holes or the plurality of brush grooves are spaced apart in a circumferential direction of the housing; and
a plurality of the conductive fiber brushes correspond to the plurality of brush through holes or the plurality of brush grooves in arrangement position.

13. The negative ion generating device according to claim 1, wherein
the driving mechanism comprises a motor having a rotating shaft;
a center of the housing defines a first motor through hole;
a center of the cleaning member defines a second motor through hole;
the motor is fixed to the housing; and
the rotating shaft passes through the first motor through hole and the motor through hole sequentially to fixedly couple to the cleaning member, to drive the cleaning member to rotate synchronously.

14. The negative ion generating device according to claim 1, wherein
the cleaning member defines a through hole or a notch at a position corresponding to the conductive fiber brush.

15. The negative ion generating device according to claim 14, wherein
the through hole has a size greater than an outer diameter of the conductive fiber brush.

16. The negative ion generating device according to claim 14, wherein
a plurality of through holes are provided, and the plurality of through holes are arranged side by side and spaced apart.

17. An air purifier, comprising:
a negative ion generating device, comprising:
a housing;
a negative ion assembly disposed in the housing, the negative ion assembly being configured to produce a negative ion, the negative ion assembly comprising a conductive fiber brush; and
a cleaning assembly disposed in the housing, the cleaning assembly comprising a driving mechanism and a cleaning member coupled to a power output end of the driving mechanism, the driving mechanism being configured to provide power, the cleaning member configured to move under action of the power provided by the driving mechanism, and contact or separate from the conductive fiber brush during movement; and
a bracket, the negative ion generating device being fixed through the bracket,
wherein the conductive fiber brush is disposed along a circumferential edge of the housing; and
the cleaning member is configured to rotate clockwise or counterclockwise around an edge of the housing in a horizontal direction under action of the power provided by the driving mechanism, and contact and separate from the conductive fiber brush during rotation.

18. The air purifier according to claim 17, wherein the air purifier further comprises a fan, the fan is rotatable to form a wind path in the air purifier, and the negative ion generating device is arranged in the wind path or outside the wind path.

19. The air purifier according to claim 17, wherein the negative ion generating device is fixed in the air purifier with a screw or snap connection.

* * * * *